United States Patent [19]

Jina et al.

[11] Patent Number: 5,526,120
[45] Date of Patent: Jun. 11, 1996

[54] TEST STRIP WITH AN ASYMMETRICAL END INSURING CORRECT INSERTION FOR MEASURING

[75] Inventors: Arvind N. Jina, Milpitas; Loren R. Larson, Fremont; John L. Smith, Los Altos, all of Calif.

[73] Assignee: LifeScan, Inc., Milpitas, Calif.

[21] Appl. No.: 302,281

[22] Filed: Sep. 8, 1994

[51] Int. Cl.⁶ ........................................................ G01N 21/47
[52] U.S. Cl. .......................... 356/446; 356/423; 356/244; 422/56; 422/58; 422/82.05; 422/82.09
[58] Field of Search .......................... 422/56, 58, 82.05, 422/82.09; 250/561; 356/244, 446, 423

[56] References Cited

U.S. PATENT DOCUMENTS

| | | | |
|---|---|---|---|
| 3,552,928 | 1/1971 | Fetter | 422/56 |
| 3,980,437 | 9/1976 | Kishimoto et al. | 356/445 |
| 3,992,158 | 11/1976 | Przybylowicz et al. | 422/58 |
| 4,042,335 | 8/1977 | Clément | 422/56 |
| 4,125,372 | 11/1978 | Kawai et al. | 422/56 |
| 4,144,306 | 3/1979 | Figueras | 422/56 |
| 4,255,384 | 3/1981 | Kitajima et al. | 422/56 |
| 4,258,001 | 3/1981 | Pierce et al. | 422/56 |
| 4,292,272 | 9/1981 | Kitajima et al. | 422/56 |
| 4,452,887 | 6/1984 | Kitajima et al. | 422/56 |
| 4,509,859 | 4/1985 | Markart et al. | 356/446 |
| 4,592,893 | 6/1986 | Poppe et al. | 422/56 |
| 4,682,895 | 7/1987 | Costello | 356/402 |
| 4,714,874 | 12/1987 | Morris et al. | 422/58 |
| 4,774,192 | 9/1988 | Terminiello et al. | 422/56 |
| 4,790,979 | 12/1988 | Terminiello et al. | 422/56 |
| 4,791,461 | 12/1988 | Kishimoto et al. | 356/446 |
| 4,816,224 | 3/1989 | Vogel et al. | 422/56 |
| 4,952,893 | 8/1990 | Cuddy | 333/81 R |
| 4,978,503 | 12/1990 | Shanks et al. | 356/244 |
| 4,994,238 | 2/1991 | Daffern et al. | 422/56 |
| 5,029,583 | 7/1991 | Meserol et al. | 128/633 |
| 5,037,614 | 8/1991 | Makita et al. | 356/402 |
| 5,059,394 | 10/1991 | Phillips et al. | 422/82.05 |
| 5,082,516 | 1/1992 | Akao et al. | 156/277 |
| 5,095,025 | 3/1992 | Tanaka et al. | 514/367 |
| 5,095,026 | 3/1992 | Schoenwald et al. | 514/367 |
| 5,120,507 | 6/1992 | Sano et al. | 422/82.05 |
| 5,167,145 | 12/1992 | Butler et al. | 356/39 |
| 5,174,963 | 12/1992 | Fuller et al. | 422/82.05 |
| 5,192,502 | 3/1993 | Attridge et al. | 356/246 |
| 5,211,914 | 5/1993 | Vogel et al. | 422/56 |
| 5,231,576 | 7/1993 | Suzuki et al. | 356/446 |
| 5,232,668 | 8/1993 | Grant et al. | 422/82.05 |
| 5,236,940 | 8/1993 | Audiau et al. | 514/367 |
| 5,246,858 | 9/1993 | Arbuckle et al. | 356/446 |
| 5,252,293 | 10/1993 | Drbal et al. | 422/56 |
| 5,277,870 | 1/1994 | Fuller et al. | 422/82.05 |
| 5,306,623 | 4/1994 | Kiser et al. | 435/14 |
| 5,316,727 | 5/1994 | Suzuki et al. | 422/82.05 |
| 5,397,537 | 3/1995 | Suzuki et al. | 422/58 |

FOREIGN PATENT DOCUMENTS

| | | |
|---|---|---|
| 0456098A2 | 11/1991 | European Pat. Off. . |
| 0574134A2 | 12/1993 | European Pat. Off. . |
| 4035052A1 | 11/1989 | Germany . |
| 4-113268 | 4/1992 | Japan . |
| 938029 | 8/1961 | United Kingdom . |
| 1037155 | 7/1966 | United Kingdom . |
| 2090659 | 7/1982 | United Kingdom . |
| WO94/18559 | 8/1994 | WIPO . |

OTHER PUBLICATIONS

Azo Dyes by Oxidative Coupling, VIII*, S. Hunig and Kobrich, Liebigs Ann. Chem 617, 216 (1958).

New Contributions to the Optics of Intensely Light–Scattering Materials, Part I; Journal of Optical Society of America, vol. 38, No. 5, May 1948, pp. 448–457.

Primary Examiner—Frank Gonzalez
Assistant Examiner—Jason D. Eisenberg

[57] ABSTRACT

For measuring an analyte in a liquid, a test strip and apparatus each have an asymmetry. The asymmetries combine to permit a test strip to be inserted into the apparatus when it is correctly aligned but prevent the test strip from being fully inserted if it is wrong side up. The apparatus also detects whether or not the strip has been fully inserted.

6 Claims, 8 Drawing Sheets

TEST STRIP WITH AN ASYMMETRICAL END INSURING CORRECT INSERTION FOR MEASURING

FIELD OF THE INVENTION

The present invention relates to a test device and method for the determination of analytes in aqueous fluids, particularly whole blood. In a specific embodiment it concerns a test device and method for optically measuring the concentration of glucose in whole blood.

BACKGROUND OF THE INVENTION

The quantification of chemical and biochemical components in colored aqueous fluids, in particular colored biological fluids such as whole blood and urine and biological fluid derivatives such as blood serum and blood plasma, is of ever-increasing importance. Important applications exist in medical diagnosis and treatment and in the quantification of exposure to therapeutic drugs, intoxicants, hazardous chemicals and the like. In some instances, the amounts of materials being determined are either so minuscule—in the range of a microgram or less per deciliter—or so difficult to precisely determine that the apparatus employed is complicated and useful only to skilled laboratory personnel. In this case the results are generally not available for some hours or days after sampling. In other instances, there is often an emphasis on the ability of lay operators to perform the test routinely, quickly and reproducibly outside a laboratory setting with rapid or immediate information display.

One common medical test is the measurement of blood glucose levels by diabetics. Current teaching counsels diabetic patients to measure their blood glucose level from two to seven times a day depending on the nature and severity of their individual cases. Based on the observed pattern in the measured glucose levels, the patient and physician together make adjustments in diet, exercise and insulin intake to better manage the disease. Clearly, this information should be available to the patient immediately.

Currently a method widely used in the United States employs a test article of the type described in U.S. Pat. No. 3,298,789 issued Jan. 17, 1967 to Mast. In this method a sample of fresh, whole blood (typically 20–40 μl) is placed on an ethylcellulose-coated reagent pad containing an enzyme system having glucose oxidase and peroxidase activity. The enzyme system reacts with glucose and releases hydrogen peroxide. The pad also contains an indicator which reacts with the hydrogen peroxide in the presence of peroxidase to give a color proportional in intensity to the sample's glucose level.

Another popular blood glucose test method employs similar chemistry but uses, in place of the ethylcellulose-coated pad, a water-resistant film through which the enzymes and indicator are dispersed. This type of system is disclosed in U.S. Pat. No. 3,630,957 issued Dec. 28, 1971 to Rey et al.

In both cases the sample is allowed to remain in contact with the reagent pad for a specified time (typically one minute). Then, in the first case, the blood sample is washed off with a stream of water while in the second case, it is wiped off the film. The reagent pad or film is then blotted dry and evaluated. The evaluation of the analyte concentration is made either by comparing color generated with a color chart or by placing the pad or film in a diffuse reflectance instrument to read a color intensity value.

While the above methods have been used in glucose monitoring for years, they do have certain limitations. The sample size required is rather large for a finger stick test and is difficult to achieve for some people whose capillary blood does not express readily.

In addition, these methods share a limitation with other simple lay-operator colorimetric determinations in that their result is based on an absolute color reading which is in turn related to the absolute extent of reaction between the sample and the test reagents. The fact that the sample must be washed, blotted or wiped off the reagent pad after the timed reaction interval requires that the user be ready at the end of the timed interval and wipe or apply a wash stream at the required time. The fact that the reaction is stopped by removing the sample leads to some uncertainty in the result, especially in the hands of the home user. Overwashing, overblotting or overwiping can give low results and underwashing can give high results.

Another problem that often exists in simple lay-operator determinations is the necessity for initiating a timing sequence when blood is applied to a reagent pad. A user will typically have pricked his or her finger to obtain a blood sample and will then be required to simultaneously apply the blood from the finger to a reagent pad while starting a timer with his or her other hand, thereby requiring the use of both hands simultaneously. This is particularly difficult since it is often necessary to ensure that the timer is started only when blood is applied to the reagent pad. All of the prior art methods require additional manipulations or additional circuitry to achieve this result. Accordingly, simplification of this aspect of reflectance reading instruments is desirable.

Great improvements have been achieved upon the introduction of the systems described in U.S. Pat. Nos. 5,179,005, 5,059,394, 5,049,487, and 4,935,346 wherein an apparatus is provided for accepting a test strip having a test pad, one surface of which comprises a reaction zone adapted to be optically readable by said apparatus. The test strip is inserted into the apparatus, the apparatus is started and then whole blood is applied onto the test pad. At least a portion of such blood is allowed to permeate to the reaction zone whereby any analyte present therein will react with color-producing reagents in the test pad to alter the light reflectivity characteristics of the reaction zone. The reflectivity of the reaction zone is then a measure of the presence and/or quantity of analyte present in the blood sample. As described in the aforementioned patents, this system does not require a large sample of blood nor does it require the user to undertake timed manipulations with respect to the beginning or end of the reaction. Instead, because the strip is first inserted into the apparatus prior to the application of the sample, a standard reflectance reading of the reaction zone in the dry state may be obtained. The beginning of the reaction can be detected by the first "breakthrough" of the liquid sample onto the reaction zone by monitoring the reflectance and comparing the reading to the standard reflectance of the dry reaction zone. A reflectance reading taken at a predetermined time after the reaction has begun and compared to the standard reflectance, i.e., the dry reaction zone reading, will be indicative of the quantity of analyte present in the sample.

While the above described system does indeed solve the problems of the prior art and relieves the user of the burden of measurement and timing, it does require that the user apply a sample of blood onto the strip while the strip is in the apparatus. For the most part this represents no problem to the vast majority of users. However, certain users suffer from handicaps such as poor vision or impaired motor coordination so that the accurate application of blood from such users' pricked fingers to the strip, in place on the apparatus, represents a hardship. Further, for institutional users, for example, there is the possibility that some quantity of blood remains on the device from a prior user, since the systems necessitate applying one's pricked finger to the device. In such instances there is the need to disinfect the device between users.

Accordingly, for the above reasons, in the case of at least some users, it would be preferable to first apply the blood sample to the strip prior to inserting the strip into the apparatus. Unfortunately, by doing so the apparatus no longer has the capability of reading reflectance of the dry, unreacted, reaction zone, i.e., at no time is the dry reaction zone presented to the apparatus. This reading was necessary in the prior devices to provide a calibration standard for determining the reflectance change as a result of the reaction and hence the presence and/or quantity of the analyte in the sample.

In a commonly assigned, copending U.S. patent application Ser. No. 302,160, filed Sep. 8, 1994, incorporated herein by reference, there is described a strip, apparatus, and methodology for allowing the user to apply a sample to the strip before inserting it into the reading apparatus while also providing a calibrated standard. This above-referenced patent application teaches a strip which comprises a portion for having the liquid applied thereto, this portion having an optically visible surface (i.e., at least with respect to the optics of the apparatus to be employed with the strip) defining a reaction zone. The reaction zone is such that its reflectance varies as a function of the quantity of analyte present in the applied liquid. Preferably, such is accomplished by the analyte, if present, reacting with reactants to produce a color change of the reaction zone. The test strip further comprises an optically visible standard zone of high reflectance, relative to the reflectance of the reaction zone. The standard zone is positioned on the strip so as to lead the reaction zone as the strip is inserted into the apparatus.

Accordingly, the apparatus may be provided with optical means for sequentially determining the reflectance value of the standard zone as the strip is being inserted into its fully inserted position in the apparatus and the reflectance value of the reaction zone after the strip has been inserted. Additionally, the apparatus is provided with means for calculating the presence and/or quantity of the analyte in question as a function of the standard zone reflectance and the reaction zone reflectance.

Owing to the configuration of the strip of this invention and specifically, the provision of a standard zone leading the reaction zone, the aforementioned apparatus need be provided with only one set of optics, e.g., one light emitting diode and one light detector for reading the reflection at a single position along the path of the strip.

In operation, the user turns on the apparatus, applies the sample to a fresh strip and then inserts the strip fully into the apparatus and reads the results. Without intervention of the user, the strip, configured as described, allows the apparatus to read the reflectance of light incident upon standard zone as it passes the optics of the apparatus as the strip is inserted. This reading is then calibrated to account for variations owing to changes in the apparatus from the factory condition and to lot-to-lot variations in the strip. The fully inserted strip thereafter presents the reaction zone to the optics of the apparatus and the reflectance of this surface may be read. Means are provided for the apparatus to calculate and report the analyte presence or concentration as a function of these readings.

The above-described system has gone a long way toward easing the user's task in determining analyte concentration. It will be appreciated, however, that it is fundamental to the successful, optical reading of a strip on which liquid has been applied, that the strip be properly oriented when inserted into the apparatus. Specifically, the strip must be inserted right side up and fully into the apparatus. In a surprising number of cases, the strip is improperly introduced upside down or not completely inserted with a resultant erroneous reading. At best, such an error, if not caught immediately, requires discarding the strip, which can be contaminated or otherwise altered in the erroneous attempt to use it upside down and repeating the process with a fresh strip. Obviously, in the case of a blood sample requiring another finger pricking, this is highly undesirable. In the worst case, the erroneous results may be accepted by the user with potentially adverse consequences.

A prior art device sold by the Boehringer-Mannheim Company under the trademark Accutrend® is provided with a black band on the trailing end of the strip. The apparatus for use with such a strip appears to be provided with two sets of optics; one to read a first zone and the second to read the black band. It appears that the apparatus is provided with microprocessing means for recording the absence of detection of such black band by the second set of optics. Such absence would be indicative of the strip having been inserted upside down.

Such a system provides some safety in insuring that the strip has been inserted right side up but does not provide sufficient safety to insure that the strip is fully inserted; i.e., the strip could buckle and record a proper reading of the back band without full insertion. Further, a failure of the optics due to an anomaly such as dirt on the strip could cause a false reading that the strip has been properly inserted.

In a commonly assigned, copending U.S. application Ser. No. 302,560, filed Sep. 8, 1994, and incorporated herein by reference, a simple method for assuring detection of a strip inserted upside down is described. In some instances, however, still greater assurance is felt to be necessary. Accordingly, there is a need to provide a system wherein the upside down insertion of a strip or failure to fully insert a strip is detected and to accomplish this with a method that provides a high degree of assurance against false positives.

SUMMARY OF THE INVENTION

In accordance with the teachings of this invention, a strip, method and apparatus are provided for determining the presence or quantity of an analyte in a liquid by inserting the strip into a passageway of a reading apparatus wherein means are provided for rapidly affirming to a high degree of assurance that the strip has been fully inserted right side up with respect to the optics of the apparatus.

Specifically, the test strip of this invention is a flat, longitudinally extending strip having first and second major surfaces, an insertion end for leading the insertion of the strip into the passageway of the apparatus and an opposite trailing end. One of said major surfaces and, preferably the first major surface, is provided at a position intermediate to the insertion end and the trailing end, with a reaction zone, i.e., an area on the first major surface readable by the apparatus when the strip is fully and properly inserted into the passageway. The reaction zone has the property of producing an apparatus-readable indication which is a function of the presence or quantity of the analyte in the liquid when a sample of the liquid is applied to the strip.

In accordance with the teachings of this invention, the extreme portion of one of said major surfaces and preferably the first surface, at the insertion end of the strip, is, firstly, provided with apparatus detectable means for cooperating with detection means at the corresponding end of the passageway of the apparatus. Accordingly, the apparatus can be programmed to determine whether or not the insertion end of the strip has reached this point in the apparatus passageway, i.e., whether or not the strip has been fully inserted. Secondly, this extreme portion of the strip at the insertion end is further provided with an asymmetrical shape (asymmetrical in the sense of not exhibiting line symmetry about the longitudinal center line of the strip). Accordingly, the passageway can be provided with a mating configuration for such asymmetrical strip portion when the strip is inserted right side up. On the other hand, should the strip be inserted wrong side up, then the asymmetry will cause the strip and passageway to interfere and prevent the strip from being fully inserted. The detectable means on the strip, cooperating with the detection means in the passageway, will then recognize the error.

As can be seen from the above description, when adhering to the teachings of this invention, it becomes essentially physically impossible to fully insert an upside down strip into the passageway and further, any strip not fully inserted (irrespective of its orientation otherwise) will be recognized by the apparatus as an error.

In a preferred embodiment, the reaction zone is a surface of a test pad containing reagents for altering the reflection properties of the reaction zone as a function of the quantity of analyte in the liquid applied to such test pad. The apparatus is equipped with an optical system for reading reflectance values of the reaction zone. Such a system is employed, for example, in determining the quantity of such analytes as glucose, cholesterol and alcohol in human blood.

In a specific embodiment, the detectable means at the extreme portion of the first surface of the strip comprises a band of material having an apparatus readable reflectance and the detection means in the apparatus comprises a source of light directed onto such band and a reflected light detector. In another specific embodiment, the detectable means on the strip comprises an electrically conductive material and the detection means in the passageway comprises two contacts and associated circuitry whereby the presence of the detectable means overlying the contacts when the strip is fully inserted closes an electrical circuit, the closing of which is monitored by the apparatus.

BRIEF DESCRIPTION OF THE DRAWINGS

The present invention can be more readily understood by reference to the following detailed description when read in conjunction with the attached drawings wherein.

DETAILED DESCRIPTION OF THE INVENTION

Figure 1:
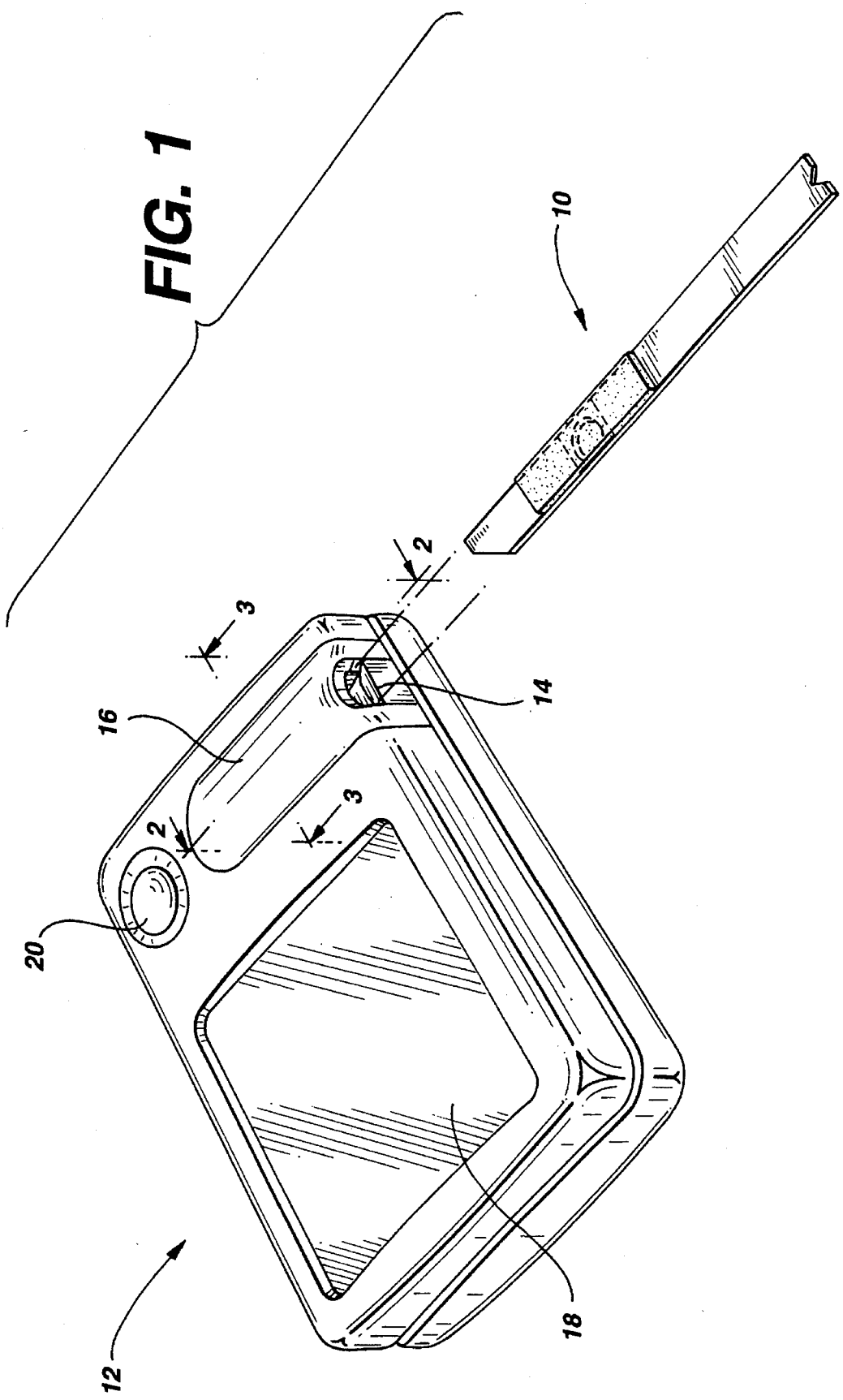
FIG. 1 is an exploded, perspective view of a strip and apparatus embodying the teachings of this invention.

Turning now to the drawings, FIG. 1 illustrates in exploded, perspective view, a strip 10 for applying a sample thereon and for inserting such sample laden strip 10 into an optical reading apparatus 12. The embodiments of the strip 10 and apparatus 12 will generally be described hereinafter in terms of detection and quantification of glucose but it will be understood by those skilled in the art that the teachings herein are not limited to glucose determinations, and instead may be applied to other analyte determinations. Further, for the purposes of simplification and clarity, the strip 10, the apparatus 12 and their respective component parts shall all be described as being in the orientation shown in the drawings and terms such as "the bottom" and "the top" shall be employed consistent with such orientation. It will be appreciated, however, that this method of description is merely convenient and that in no way is the invention restricted to such orientation and, in fact, the strip and strip holder may be rotated through any angle relative to the apparatus and the teachings herein shall still apply.

Figure 2:
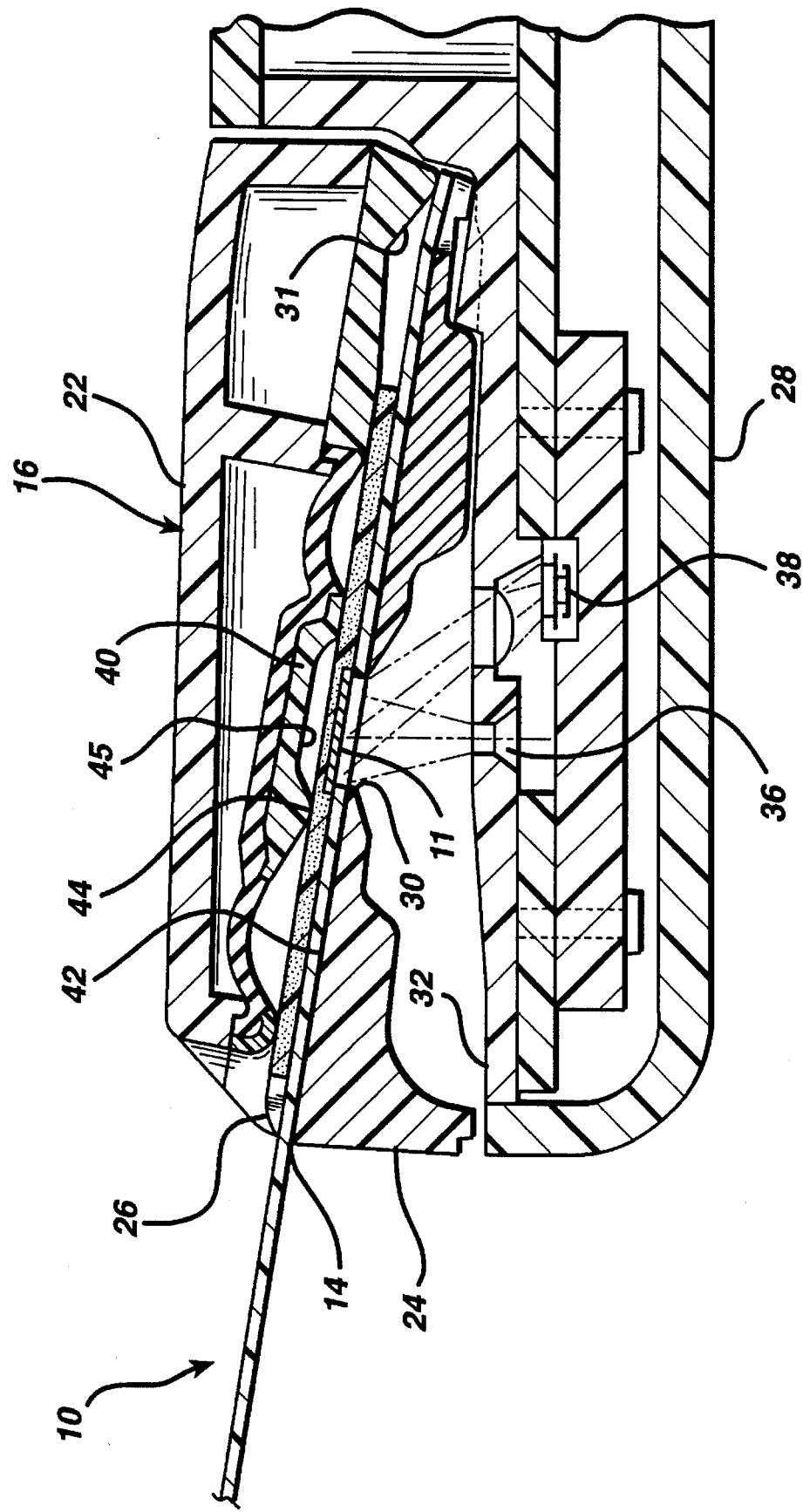
FIG. 2 is a partial, longitudinal, cross-sectional view taken along line 2—2 of FIG. 1 and illustrating the strip fully inserted into the apparatus.
Figure 3:
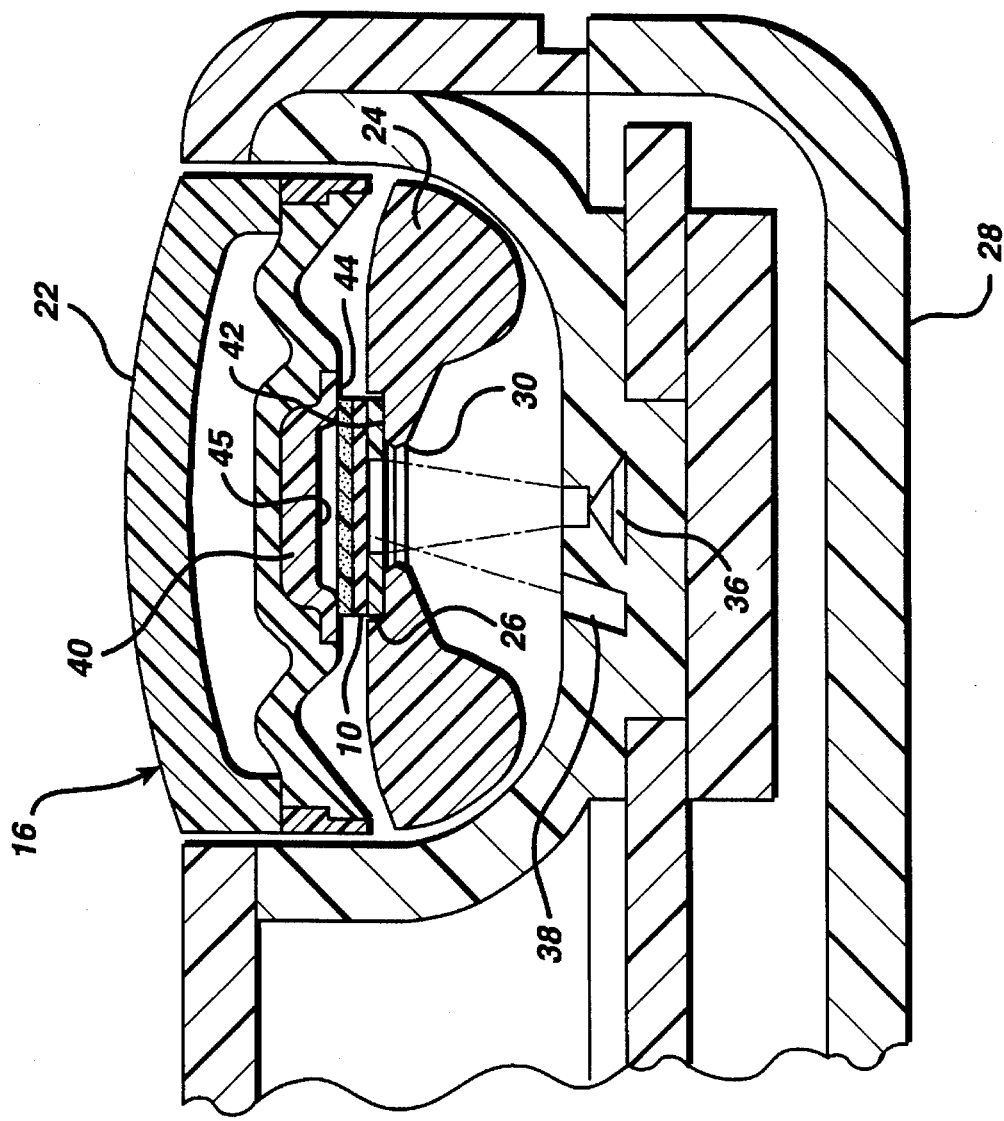
FIG. 3 is a partial, transverse, cross-sectional view, taken along line 3—3 of FIG. 1 and illustrating the strip fully inserted into the apparatus.

As can be seen in FIG. 1, the strip 10 is adapted to be inserted longitudinally, into an opening 14 of a strip holder 16 carried on apparatus 12. Strip holder 16, shown in more detail in FIGS. 2 and 3, is preferably removable from apparatus 12 for cleaning. The apparatus 12 is provided on its visible surface with a screen 18 on which messages, instructions, error warnings, and most importantly, results may be displayed by means such as liquid crystal displays as are well known in the art. Such information may be conveyed by letters, words, numbers or icons. Additionally, apparatus 12 is provided with a power switch for activating the apparatus, preferably with batteries and such power switch is shown as push button 20 on the drawings.

Referring now to FIGS. 2 and 3, illustrated therein in longitudinal and transverse cross-sectional views respectively, is the removable strip holder 16 with a strip 10 fully inserted therein, together with fragmentary views of the adjacent parts of the apparatus 12. The strip holder 16 is comprised of an upper guide 22 and a lower guide 24 which together form a channel or strip passageway 26 into which the strip is inserted via opening 14. The extent of insertion of the strip is determined by strip impeding wall 31, which, in accordance with the teachings of this invention is designed to mate with the shape of the insertion end of the strip when the strip is properly inserted and to interfere with the insertion end of the strip when the strip is inserted upside down. It should be noted that the passageway 26 is canted at an angle with respect to the plane of the bottom 28 of the apparatus 12, so as to facilitate the insertion of strip 10 into the apparatus when the apparatus is sitting on a flat surface.

The lower guide 24 is provided with an aperture 30 through which the bottom major surface 11 of the strip 10 can be "seen" by the optics located below lower guide 24. As will be understood hereinafter, the aperture 30 is positioned along the lower guide 24 so as to "see" the bottom surface of a reaction zone of strip 10 when the strip 10 is fully inserted into passageway 26.

The optics for the apparatus are located in optic block 32 affixed to apparatus 12. Optic block 32 contains a light emitting diode (LED) 36 capable of directing light through aperture 30, upon a surface such as the lower surface 11 of the strip. The light emitting diode is preferably one which emits light of essentially a uniform wavelength in rapid bursts for a period of time, each time it is activated. For the purposes of glucose determination it has been found preferable to employ two such LED's, each emitting light at a different wavelength and preferably at 660 and 940 nanometers (LED 660 and LED 940, respectively). The optic block 32 also comprises a photodetector 38, a device capable of intercepting light reflected from the surface upon which the LED's focus and converting such light into a measurable voltage.

Incorporated into the upper guide 22 is bias means 40 which is adapted to be biased toward the upper surface 42 of the lower guide in the area of the aperture 30 so as to ensure that the portion of the strip 10 lying over the aperture 30 is flat and presents an optically consistent surface to the optics. As illustrated in the drawings, bias means 40 comprises an elastomeric membrane having, on its surface opposing the aperture, a ring-like projecting gasket 44 which is adapted to bear against the strip when in place and hold the strip flat to the aperture. Centered within the ring-like projection is a colored target, preferably gray, hereinafter referred to as the "gray target" 45. The gray target 45 presents to the optics a surface for assuring the correct calibration of the apparatus before the strip is inserted. Additionally, it is the gray target that is "seen" by the optics once the apparatus is turned on and before a strip is inserted.

Figure 15:
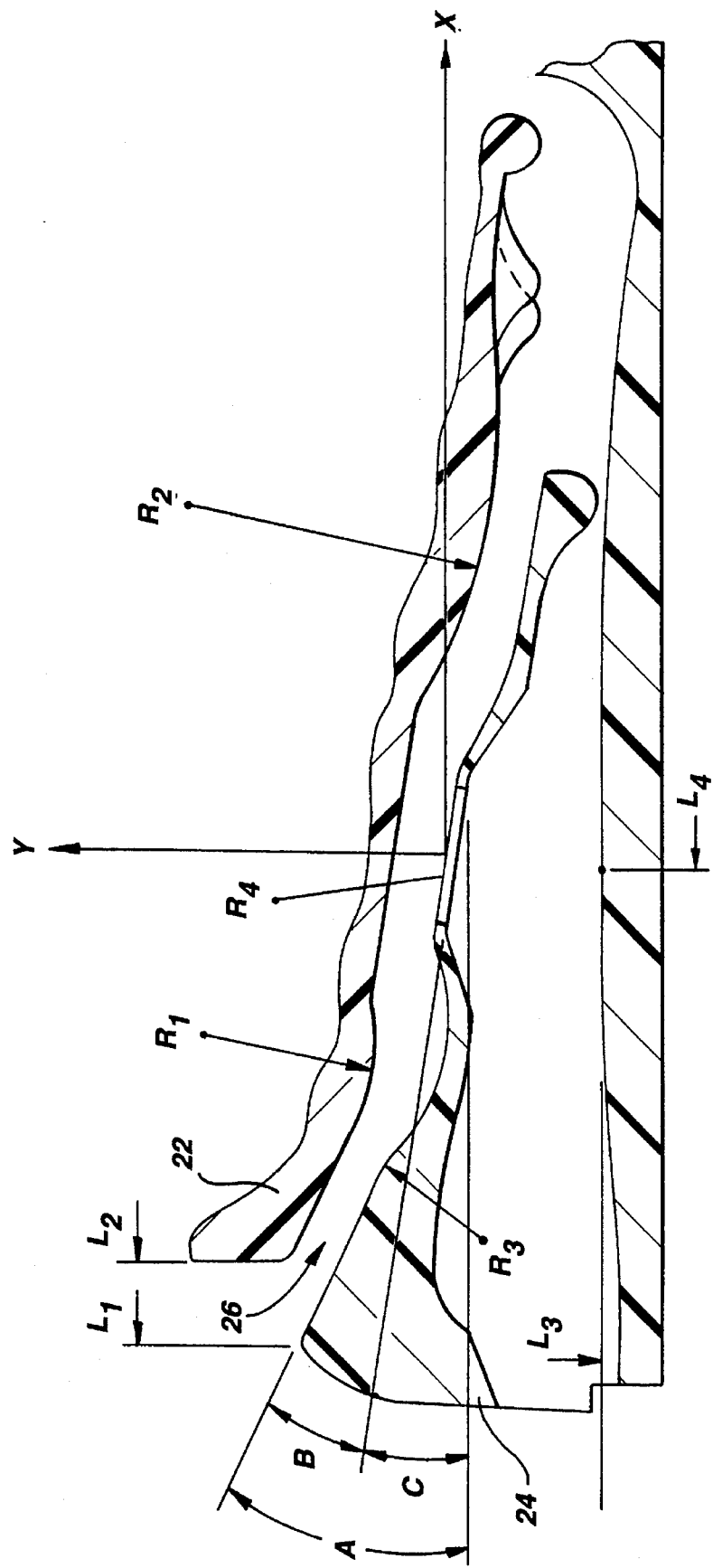
FIG. 15 illustrates a detail of a strip passageway shown in longitudinal cross-section.

The bias means 40 may take forms other than that of an elastomeric membrane. For example, a leaf spring can be used as such bias means. In a copending, commonly assigned U.S. patent application Ser. No. 302,282, filed Sep. 8, 1994, (incorporated herein by reference), such alternative bias means are described and include a particularly useful means in which the passageway 26 is designed in a serpentine configuration which, in combination with a strip having spring properties, serves to function as a bias means. Such a passageway is illustrated in FIG. 15 wherein upper guide 22 and lower guide 24 are shown. TABLE 1 below recites preferred dimensions for the angles, distances and radii; all based on the x,y coordinates shown in the Figure.

TABLE 1

| DIMENSIONS FOR FIG. 15 | |
|---|---|
| ANGLES (Degrees) | |
| A | 26 |
| B | 17 |
| C | 9 |
| DISTANCES (Inches) | |
| $L_1$ | 0.562 |
| $L_2$ | 0.467 |
| $L_3$ | 0.184 |
| $L_4$ | 0.013 |
| CURVATURE | |
| RADIUS (Inches) | CENTER (X,Y In) |
| $R_1$  0.2 | 0.207, 0.179 |
| $R_2$  0.347 | 0.391, 0.300 |
| $R_3$  0.100 | 0.417, 0.006 |
| $R_4$  2.635 | 0.412, 2.603 |

Figure 4:
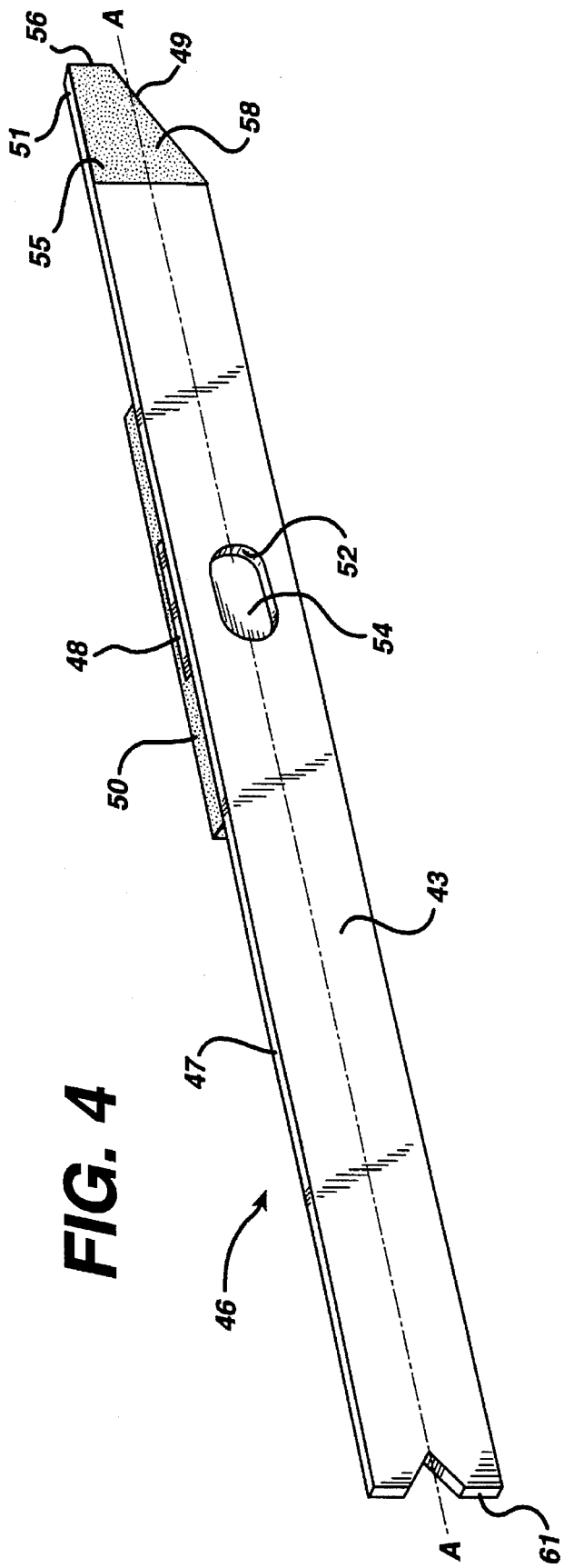
FIG. 4 is a perspective view illustrating a strip of this invention.

Referring now to FIG. 4 illustrated therein is a perspective view of the bottom major surface 43 of a strip 46 embodying the teachings of this invention.

This embodiment is described herein in terms of being employed for detecting glucose in whole blood, it being understood that the general teachings herein are applicable to detecting any analyte in liquids.

The strip 46 comprises an elongate and generally rectangular support 47 onto which is attached a test pad 48 containing reactants and provided with an overlying transport medium 50. In use the sample is to be applied to the top surface of the transport medium 50 overlying the test pad 48. A portion of the sample penetrates through the test pad and any glucose present reacts with the reactants therein to produce a color change which is visible on the bottom surface of the test pad. A support aperture 52 is provided through the support for aligning with aperture 30 in the lower guide of the apparatus when the strip is fully inserted therein, so that a portion of the bottom of the surface of the test pad will be visible to the optics of the apparatus (such portion hereinafter, the reaction zone).

Details of these components of the strip are described in copending U.S. Ser. No. 881,970, filed on May 12, 1992, and incorporated herein by reference. Briefly, the transport medium 50 comprises pores which draw the sample therethrough by capillary action. The transport medium may be composed of natural materials such as cotton or paper, as well as such synthetic materials as polyesters, polyamides, polyethylene and the like.

The transport medium has pores having an effective diameter in the range of about 20 microns to about 350 microns, preferably about 50 to about 150 microns, e.g., 100 microns. The transport medium is generally hydrophilic or may be rendered hydrophilic by treatment with surfactants compatible with red blood cells. One such compatible surfactant is MAPHOS™ 66 sold by Mazer Chemical, a division of PPG Industries Inc. Chemicals of Gurnee, Ill. In a preferred embodiment, the transport medium is capable of absorbing blood samples of up to about 20 to about 40 microliters e.g., 30 microliters.

The transport medium may be, for example, a filter paper or sintered plastic material, such as those porous polyethylene materials commonly available from the Porex Corp. of Fairburn, Ga. The transport medium is generally fabricated to have a thickness of about 0.022 inch, with about 0.25 inch width and about 1.0 inch length. The transport medium is treated with a red blood cell compatible surfactant solution. Since only about 3 to about 5 microliters of blood are required to saturate the testing pad, the transport medium will preferably possess a small void volume in order not to require large volumes of blood. Excess blood applied to the reagent strip is absorbed and held in the portion of the transport medium which extends beyond the test pad.

The test pad and its preparation are also set forth in detail in U.S. Pat. No. 4,935,346 and need not be described in detail herein. Essentially, the test pad is a hydrophilic porous matrix to which reagents may be covalently or non-covalently bound. Examples of a suitable material include polyamides, which are conveniently condensation polymers of monomers of from 4 to 8 carbon atoms, where the monomers are lactams or combinations of diamines and di-carboxylic acids, polysulfones, polyesters, polyethylene, and cellulose based membranes. Other polymeric compositions may also be used. Further, the polymer compositions may be modified to introduce other functional groups so as to provide for charged structures, so that the surfaces may be neutral, positive, or negative, as well as neutral, basic, or acidic. The material of choice is a hydrophilic, anisotropic polysulfone membrane having pores varying in size from large to small through the thickness of the matrix. The preferred matrix is obtained from the Memtec America Corporation of Maryland and has an average pore size ranging from 0.34 to 0.4 micrometers e.g., 0.37 and a thickness of from about 125 to about 140 micrometers e.g., 130 micrometers. The ratio of the average diameter of the large to the small pores is about 100.

The transport medium 50 is attached to the test pad 48 by an adhesive layer (not shown). Suitable adhesives for this purpose, including acrylic, rubber, and ethylene vinyl acetate (EVA) based formulations. A hot melt adhesive such as those known in the art, is preferred.

The adhesive may be placed in continuous stripes located only near the perimeter of the test pad, leaving a central portion of the receiving surface of the test pad substantially unobstructed.

Alternatively, when the transport layer is composed of a material that fuses at industrially practical temperatures, the transport layer may be attached directly to the test pad by an application of heat and pressure. The transport layer is heated until it begins to melt and then pressed against the testing pad and cooled. Direct attachment of the transport layer to the testing pad by fusion obviates any need for a distinct adhesive layer.

The adhesive layer connects the transport medium to the sample receiving surface of the test pad. The transport medium is adapted to accept a whole blood sample and transport a detectable portion of the sample to the receiving surface by capillary action. The transport medium preferably extends past one or more ends of the test pad so as to form a reservoir for holding excess amounts of blood sample which may be present during actual use. It is usually more desirable to retain such excess amounts of the blood sample in the transport medium, rather than allowing the excess to drip upon the user or upon the viewing means in an uncontrolled fashion. Accordingly, it is preferred that the transport medium be capable of holding from about 20 to about 40 microliters of blood, preferably about 30 microliters of blood and of passing from about 3 to about 5 microliters of blood to the test pad.

The test pad is impregnated with a color forming reagent system specific to an analyte. Typical analytes are glucose, cholesterol, urea, and many others which will readily occur to those skilled in the art. Preferably, the color forming reagent system includes an enzyme which selectively catalyzes a primary reaction with the analyte of interest. A product of the primary reaction may be a dye which undergoes a change in color that is detectable at the reaction zone. Alternatively, the product of the primary reaction may be an intermediate which undergoes another reaction, preferably also enzyme catalyzed, and participates in a secondary reaction which, directly or indirectly, causes a dye to undergo a change in color which is detectable at the reaction zone.

An exemplary color-forming reagent system is the system which is specific to glucose and contains glucose oxidase, a peroxidase, and an oxidizable dye. Glucose oxidase is an enzyme, usually obtained from *Aspergillus Niger* or Penicillium, that reacts with glucose and oxygen to produce gluconolactone and hydrogen peroxide. The hydrogen peroxide so produced, catalyzed by a peroxidase enzyme such as horseradish peroxidase, oxidizes a dye. The resulting chromophore (the oxidized dye) exhibits a color that may be observed at the reaction zone. Many suitable oxidizable dyes are known in the art including, for example, those set out in U.S. Pat. No. 5,304,468 incorporated herein by reference. One particularly useful oxidizable dye is the 3-methyl-2 benzothiazolinone hydrazone hydrochloride/8-anilino 1-naphthalenesulfonate dye couple (MBTH/ANS couple) described in copending U.S. patent application Ser. No. 245,940, filed May 19, 1994 (LFS 30). Many other suitable color-forming reagent art. A dye couple of choice is a derivative of MBTH, meta[3-methyl 2-benzothiazolinone hydrazone] N-sulfonyl benzenesulfonate monosodium coupled with ANS. This application Ser. No. 302,575, filed Sep. 8, 1994, and incorporated hereby by reference.

The support 47 may be of a material having the properties of being sufficiently rigid to be inserted into the apparatus without undue bending or kinking. Preferably, such support is comprised of materials such as polyolefins (e.g., polyethylene or polypropylene), polystyrene or polyesters. A preferred material is the polyester available from the Imperial Chemical Industries, Ltd. of the United Kingdom and sold by them under the trademark "Melinex 329" having a thickness of about 0.014 inches.

Referring to FIG. 4, the bottom surface of the strip (i.e., the surface to be inserted in face-to-face relationship with the aperture 30 of the lower guide of the apparatus and hence the surface "seen" by the optics of the apparatus), presents a reaction zone 54 comprising the portion of the test pad 48 visible through the support aperture 52. The reaction zone 54 is longitudinally placed between the leading insertion edge 56 of the strip (leading with respect to insertion into the apparatus) and the opposite trailing edge 61.

It will now be appreciated that in order to get a proper reading of the reaction zone by the optics of the apparatus, the reaction zone must be in proper alignment with the aperture 30 in the passageway; i.e., the strip must be fully inserted into the passageway 26 right side up so that the reaction zone is in face to face relationship with aperture 30.

In accordance with the teachings of this invention, this is assured by two provisions. Firstly, the extreme portion of the bottom surface at the insertion end of the strip is provided with apparatus-detectable means 58 for cooperating with detecting means located at the corresponding end of the passageway of the apparatus. Secondly, the correct positioning of the strip is assured by combining the apparatus-detectable means and its complimentary detection means in the apparatus (hereinafter collectively "detection system") with the feature of an asymmetrical strip.

The detection system may be any of several which will occur to those skilled in the art based on the teachings herein. It has been discovered that a particularly useful combination is where the apparatus-detectable means 58 comprises a material which is electrically conductive.

The detection means in the passageway of the apparatus may then comprise two electrical contacts and associated circuitry, the electrical contacts being positioned in the passageway so that the detectable means will overly these contacts when the strip is fully inserted and close the circuit, the closing of which can be monitored by the apparatus. Such a system is more fully described in connection with FIGS. 5–8 hereinafter. The detectable means having the above-described electrical conduction properties can be comprised of any material capable of conducting such as metallic or carbon based conductive inks or blends of conductive/resistive materials as well as conductive polymers (e.g., polyaniline, polypyrrole, polyacetylene, or polythlophene) conductive polymers doped with a metal, semiconductor (e.g. zinc oxide) or metallic adhesive film or the like. Such materials may be applied to the herein prescribed region of the strip by any suitable method. Accordingly, depending on the nature of the conductive material chosen, the material may be screen printed, flexographically applied, rotogravured, painted, laminated, layered, sputtered, vapor deposited, or even insert molded onto the strip. Since the strip is preferably a polymeric film, the material may be incorporated into the starting polymer of the strip itself or impregnated therein at some point in the strip forming process.

In an alternative embodiment, the detection system can comprise providing the prescribed region of the strip with a material which has reflective properties in marked contrast to the reflective properties of the passageway when the strip is not present (i.e., the reflectance of the empty passageway). In such case, the end of the passageway may be provided with a set of optics; i.e., a light source such as a light emitting diode (LED) in combination with a reflected light detector such as those described herein for measuring the reflection of the reaction zone of the strip. Thus, for example, if the prescribed region of the strip is light in color, and hence, highly reflective as compared to an essentially black interior of the passageway, the contrast in reflected light can be recognized by the LED/light detector detection means of the apparatus. As has been described in the above referred to copending U.S. patent application Ser. No. 302, 160, for reasons of calibrating the reaction zone reflectance readings, it is highly advantageous to provide the entire portion of the bottom surface of the strip leading the reaction zone into the apparatus with a contrasting reflectance property. Accordingly, such a leading area of the bottom surface will serve as the detectable means.

The desired contrasting reflectance of the detectable means may be achieved on a strip of this invention by any number of ways as will occur to one skilled in the art. For example, the support may have laminated to it, in the desired region, a layer having the requisite reflectance. Alternatively, the material comprising the support may have incorporated therein a coloring material imparting the proper reflectance to the region comprising the detectable means.

As further alternatives, the coloring material may be printed or painted onto the appropriate region.

The method chosen for accomplishing the contrasting reflectance values between the detectable means of an inserted strip and the passageway in the absence of the strip is not critical. It is, however, important that at least a minimal contrast between these two reflectance values be exhibited to the detection means of the apparatus. Accordingly, the lower reflectance value should be no more than 0.9 times the higher reflectance value and, preferably, no more than 0.5 times.

Figure 4A:
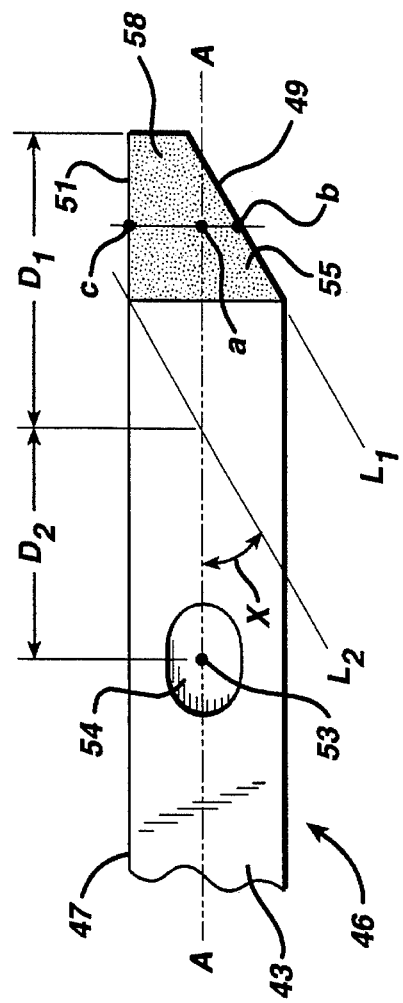
FIG. 4a is a plan view of a part of a major surface of the strip of FIG. 4.

Referring to FIG. 4a, in a preferred embodiment, the detectable means 58 are optimally located with respect to the reaction zone 54. Specifically, the portion 54 of the reaction zone readable by the apparatus comprises a centerpoint 53, centrally located on the longitudinal centerline A—A. The detectable means 58 are located within the area 55, which area 55 is defined by two parallel lines, $L_1$ and $L_2$, at an angle X with the longitudinal centerline. The angle X has a value of about 45°. The lines $L_1$ and $L_2$ are spaced apart by a distance of $D_1$, which is preferably about 0.32 inches. $L_2$, the line closest to the centerpoint 53, is at a distance $D_2$ from the centerpoint, the distance being taken along the longitudinal centerline. $D_2$ is preferably about 0.52 inches.

The strip with apparatus detectable means is further provided with the feature of asymmetry to assure proper insertion. As described herein, this asymmetry refers to providing that the extreme portion of the strip at the insertion end is given an asymmetrical shape in the sense that there is no line symmetry about the longitudinal centerline, A—A in FIG. 4. Thus, it can be seen from the embodiment shown in FIG. 4 that this insertion end comprises a region wherein, at a given point (e.g., point a), on the longitudinal center line A—A, the normal distance to a first longitudinal edge 49 (distance a–b) is less than the normal distance to the second edge 51 (distance a–c). This is accomplished in the embodiment shown in FIGS. 4–8 by simply sloping the edge 49 at an angle toward the centerline. This is also accomplished by the configuration shown in FIGS. 9–12 wherein a rectangular "corner" is cut out of the insertion end of the strip. It will be apparent to those skilled in the art that, based on the teachings herein, many other shapes may be given to the strip in this region to conform to the prescription herein including curved edges, notched edges or combinations of any of these configurations.

Figure 5:
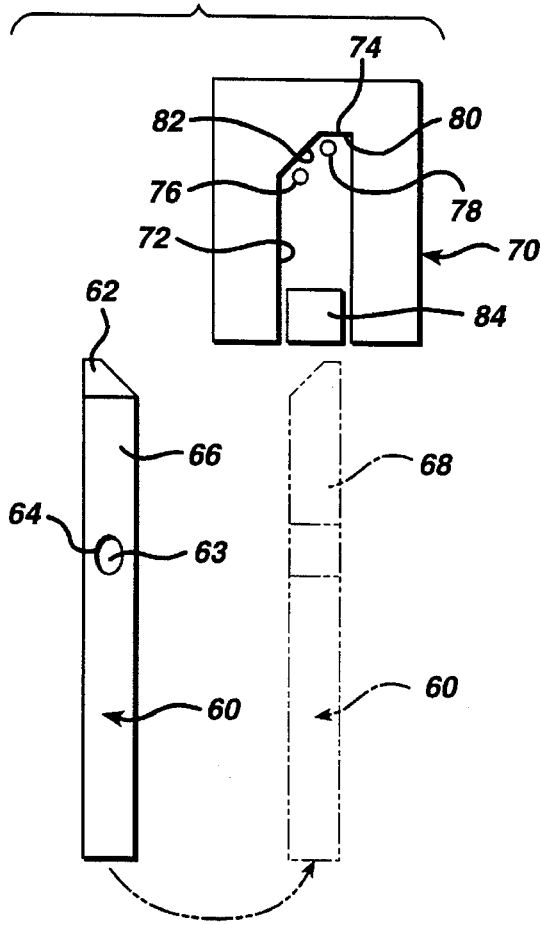
FIG. 5 is a schematic, composite, planar view of a first embodiment of a strip of this invention and the passageway of an apparatus useable in conjunction with the strip, prior to inserting the strip into the passageway.

The features of providing a strip with an apparatus-detectable means and an asymmetrical configuration at the insertion end thereof combine to assure that when such a strip is employed in an apparatus having appropriate detection means and a mating passageway, a reading of an improperly inserted strip is not possible. This is illustrated in the embodiment schematically illustrated in FIGS. 5–8. Shown in FIG. 5 is strip 60 exhibiting detectable means 62 and support aperture 64. The bottom major surface 66 is viewed in the full lined schematic view on the left and the top major surface 68 is shown in the phantom line view on the right. In this embodiment, the detectable means 62 comprises an electrically conductive surface. Also shown in FIG. 5 is the complementing portion of an apparatus 70 wherein the passageway 72 at its end 74 contains two contacts 76, 78 (with associated circuitry not shown) as the detection means. Strip 60 is provided with the same asymmetry described in connection with FIG. 4 and, accordingly, the end of passageway 72 is provided with strip impeding walls 80, 82 which mate with the insertion end of strip 60 when the strip is properly inserted. Passageway 72 is also provided with optics 84 for reading the reaction zone 63.

Figure 6:
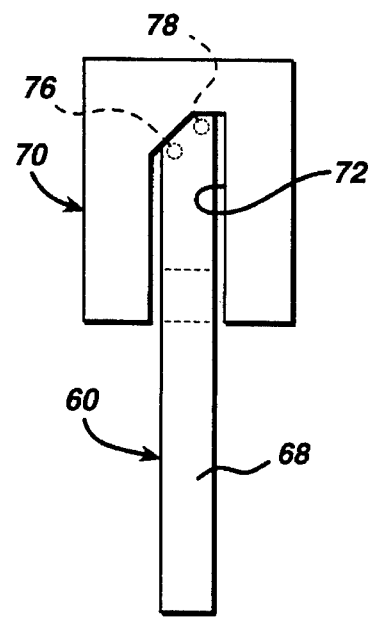
FIG. 6 is a schematic, composite, planar view of the strip and passageway of FIG. 5 wherein the strip is correctly inserted into the passageway.

Referring now to FIG. 6, it can be seen that strip 60 is properly and fully inserted into passageway 72. Accordingly, detectable means 62 now overlies contacts 76 and 78 closing the electrical circuit. The apparatus may be provided with microprocessing means for recognizing the closing of the electrical circuit and, hence, allowing further reading of the strip to continue.

Figure 7:
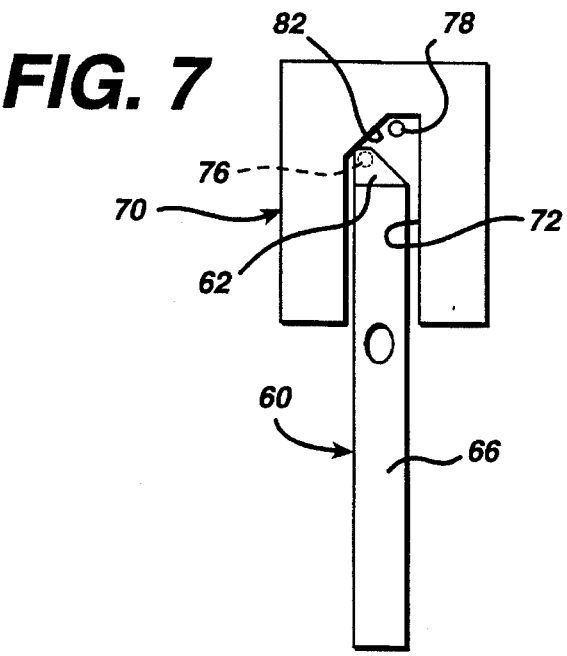
FIG. 7 is a schematic, composite, planar view of the strip and passageway of FIG. 5 wherein the strip is inserted upside down.

Referring to FIG. 7, illustrated therein is a strip 60 inserted into passageway 72 upside down. In this instance, owing to the asymmetry of the strip in conjunction with the mating confirmation of the passageway of the apparatus, wall 82 interferes with the full insertion of the strip. Accordingly, the detectable means 62 does not overlie contacts 76 and 78, and the electrical circuit is not closed. Microprocessing means provided in the apparatus fail to detect a closed circuit and may then preclude an erroneous reading of the strip. Preferably, such detected error is also reported by microprocessing means to a user readable display.

Figure 8:
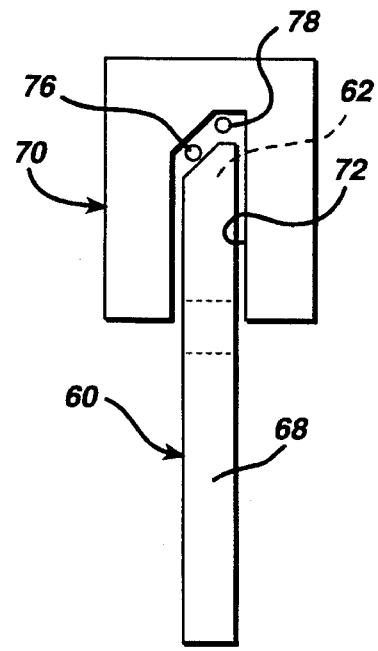
FIG. 8 is a schematic, composite, planar view of the strip and passageway of FIG. 5 wherein the strip is inserted right side up but not completely into said passageway.

Referring to FIG. 8, illustrated therein is a strip 60 which, while being inserted right side up, has not been fully inserted. Again, the detectable means 62 fails to overlie contacts 76 and 78 and, hence, the electrical circuit is not closed. Once again, microprocessing means will preclude an erroneous reading and, preferably, report the same to the user.

Figure 9:
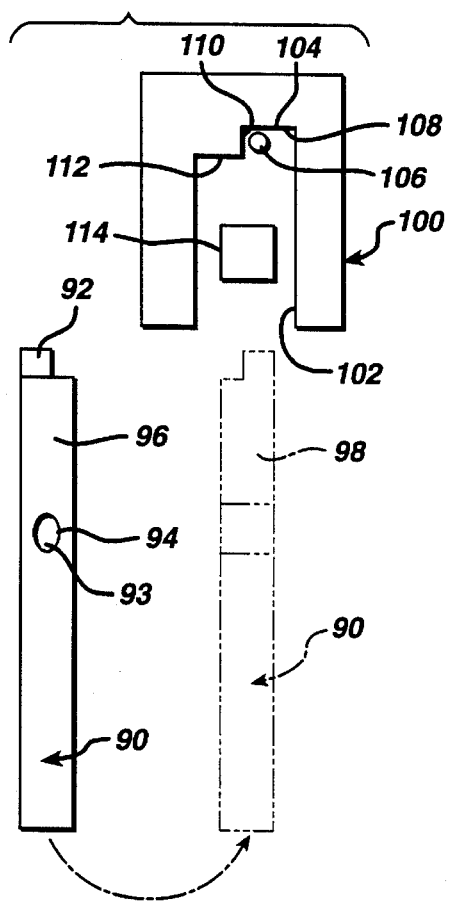
FIG. 9 is a schematic, composite, planar view of a second embodiment of a strip of this invention and the passageway of an apparatus usable in conjunction with such strip, prior to inserting the strip into the passageway.

FIGS. 9–12 illustrate another embodiment of the invention. Shown in FIG. 9 is a strip 90 exhibiting detectable means 92 and support aperture 94, with the bottom major surface 96 viewed full lined on the left and the top major surface 98 shown in the phantom lined view on the right. In this embodiment, the detectable means 92 comprises a surface having light reflective properties contrasting with those of the passageway of the apparatus when the strip is not present, i.e., detectable means 92 present a light surface in contrast to a dark surface for the walls of the passageway. Also shown in FIG. 9 is a complementary portion of an apparatus 100 wherein the passageway 102 at its end 104 contains a detection means 106 which comprises an LED/light detection combination. Strip 90 is provided with the asymmetry described above, i.e., a "corner" is cut from the insertion end of the strip. Accordingly, the end of passageway 102 is provided with strip impeding walls 108, 110 and 112 which mate with the insertion end of strip 90 when the strip is properly inserted. Passageway 102 is also provided with optics 114 for reading reaction zone 93.

Figure 10:
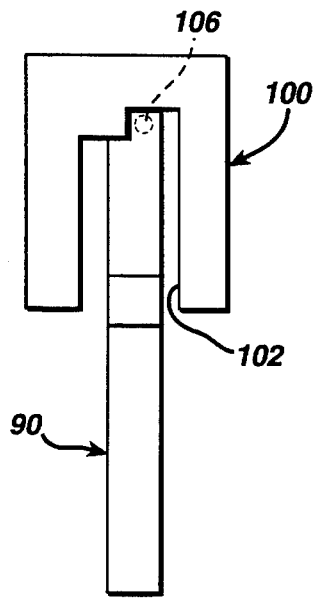
FIG. 10 is a schematic, composite, planar view of the strip and passageway of FIG. 9 wherein the strip is correctly inserted into the passageway.

Referring now to FIG. 10, it can be seen that strip 90 is properly and fully inserted into passageway 102. Accordingly, light detectable means 92 overlies the optics of detection means 106 which detects a highly reflective surface. The apparatus may be provided with microprocessing means for recognizing this detected highly reflective surface and, hence, allowing the further reading of the strip to continue.

Figure 11:
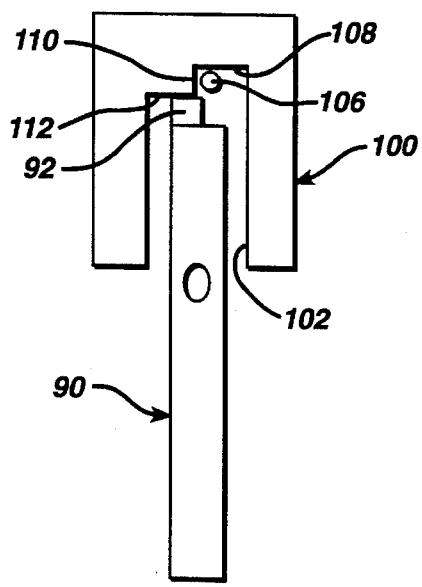
FIG. 11 is a schematic, composite, planar view of the strip and passageway of FIG. 9 wherein the strip is inserted upside down.

Referring to FIG. 11, illustrated therein is a strip 90 inserted into passageway 102 upside down. In this instance, owing to the asymmetry of the strip in conjunction with the mating configuration of the passageway of the apparatus, walls 108, 110, and 112 interfere with the full insertion of the strip. Accordingly, the detectable means 92 does not overlie the optics of detection means 106 and no highly reflective surface is detected. Microprocessing means provided in the apparatus fail to detect a highly reflective surface and may then preclude an erroneous reading of the strip and report the error to the user, using an apparatus display.

Figure 12:
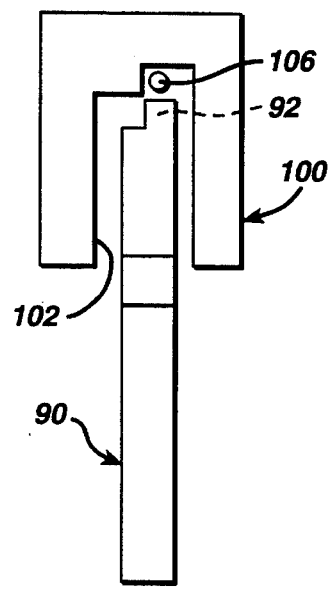
FIG. 12 is a schematic, composite, planar view of the strip and passageway of FIG. 9 wherein the strip is inserted right side up but not completely into said passageway.

Referring to FIG. 12, illustrated therein is a strip 90 which, while being inserted right side up, has not been fully inserted. Again, the detectable means 92 fail to overlie the optics of the detection means 106 and, hence, no highly reflective surface is detected. Once again, microprocessing means will preclude an erroneous reading and preferably report the same error to the user.

It will be appreciated that for the embodiments illustrated in FIGS. 9–12, the detectable means was chosen to be highly reflective and was coupled with a dark passageway. The opposite is also possible wherein the detectable means is dark and a light target, for example, is provided in the passageway. In such case, the microprocessor would be programmed accordingly.

Figure 13:
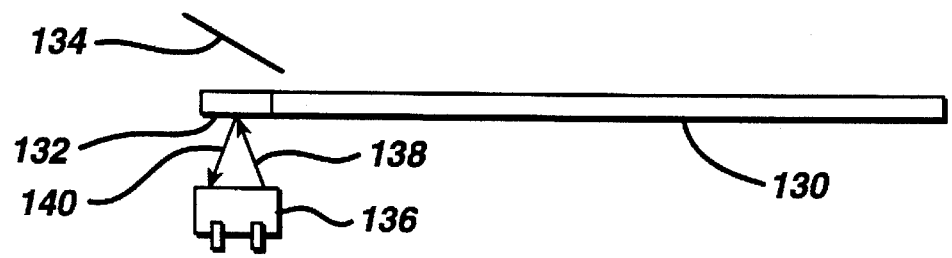
FIG. 13 is a schematic, composite, planar view of the strip and passageway of FIG. 10 illustrating the detecting means in the apparatus.
Figure 14:
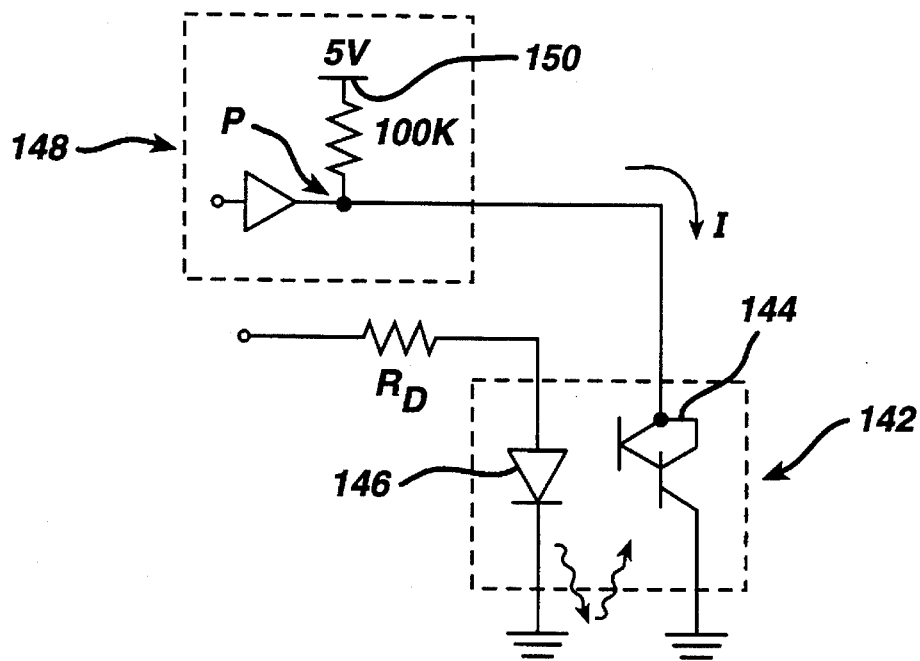
FIG. 14 is a schematic illustration of the circuitry for the detecting means of FIG. 13.

Referring to FIGS. 13 and 14, illustrated schematically therein, is the operation of a detectable means of the kind employing surface reflectance as the monitored characteristic and detection means in the passageway of a complementary apparatus employing a transistor switch coupled with circuitry. FIG. 13 illustrates the strip 130 having a highly reflectance surface as the detectable means 132. Surface 134 represents the low reflective surface "seen" by detection means 136 in the absence of the strip in the passageway of the apparatus. Detection means 136 comprises an LED emitting light symbolized by arrow 138 and light detection means for detecting reflected light, symbolized by arrow 140. Detection means 136 also comprises a switch 142 containing transistors 144, 146, which when energized by observing reflected light 140 conduct and cause a current (shown as "I") to flow. Detection means 136 also comprise an application specific integrated circuit (ASIC) 148 comprising a low voltage power source and a node P, at which voltage is monitored.

Accordingly, when no strip is present in the passageway or the strip is not fully inserted, then light reflectance 140 from surface 134 is low, essentially no current flow in switch 142 and the node P is at a relatively high potential. Under these conditions, the microprocessor of the apparatus will preclude an erroneous reading.

On the other hand, when the strip is in place, substantial reflected light 140 energizes the transistors, current flows in switch 142 and the node P is pulled to a low potential. This triggers the microprocessor to allow the reading of the strip to continue.

It will be understood that while the above embodiment is described in terms of having the detectable means 132 comprise a highly reflective surface and surface 134 to be of low reflectance, the opposite is also possible. In other words, detectable means 132 may be of a low reflectance surface and surface 134 may be of high reflectance. Accordingly, when the apparatus is turned on and before the strip is inserted, the switch is energized by receiving substantial reflected light. Once the strip is properly inserted, such reception ceases and current abates. Accordingly, the microprocessor may be programmed to only permit further reading of the strip upon such abatement of the current.

Having now fully described the invention, it will be apparent to one of ordinary skill in the art that modifications and changes can be made thereto without departing from the spirit or scope of the invention as defined by the following claim:

What is claimed is:

1. A longitudinally extending test strip for measuring an analyte in a liquid by inserting said test strip into a passageway of a reading apparatus;

said test strip having first and second major surfaces, and an insertion end for leading the insertion of the strip into said passageway and an opposite trailing end;

said passageway having a corresponding end for receiving the insertion end of the strip;

said first major surface having, positioned between said insertion end and said trailing end, a reaction zone, a portion of which is readable by the apparatus when the strip is fully inserted into said passageway;

said reaction zone producing an apparatus readable indication as a function of the analyte in said liquid when a sample of said liquid is applied to said strip;

the insertion end having apparatus detectable means for cooperating with detection means at the corresponding end of the passageway; whereby the apparatus can be programmed to determine whether or not the strip has been fully inserted therein;

the insertion end being asymmetrical with respect to a longitudinal centerline of the strip for cooperating with a mating configuration for the passageway of the apparatus, whereby said strip cannot be fully inserted when upside down;

the apparatus detectable means comprising an area having a predetermined reflectance; and said passageway having, when it is empty, a reflectance that is either less than 0.9 or more than 1.1 times the predetermined reflectance of the area of the apparatus detectable means.

2. The strip of claim 1 wherein the empty passageway reflectance is either less than 0.5 or more than 2 times the apparatus detectable area reflectance.

3. The strip of claim 1 wherein said apparatus detectable means comprise electrically conductive material for cooperating with electrical circuitry detection means in said apparatus.

4. The strip of claim 1 wherein said portion of the reaction zone readable by the apparatus comprises a centerpoint, centrally located on the longitudinal center line of the strip; and said detectable means is within an area defined by two parallel lines at an angle of 45° with the longitudinal centerline of the strip, said parallel lines, one of which is closer to the centerpoint than the other, being spaced apart a distance of 0.32 inches, wherein the distance, along the longitudinal centerline of the strip, between the centerpoint and the line of the parallel lines closer to the centerpoint, is 0.52 inches.

5. An apparatus for measuring an analyte in a liquid applied to a longitudinally extending test strip, by employing a test strip comprising:

first and second major surfaces, an insertion end for leading the strip into the apparatus and an opposite trailing end; said first major surface having, positioned between said insertion end and said trailing end, a reaction zone readable by the apparatus when the strip is fully inserted into said apparatus in a first orientation; said reaction zone producing an apparatus readable indication as a function of the analyte in said liquid when a sample of said liquid is applied to said strip; said strip further comprising at the insertion end of one of said major surfaces, an apparatus detectable means comprising an area having a predetermined reflectance, and said strip, at the insertion end, being asymmetrical with respect to a longitudinal centerline of the strip; wherein the apparatus comprises:

a longitudinally extending passageway having an open end for the insertion of the strip and an opposed end;

said passageway having, when it is empty, a reflectance that is either less than 0.9 or more than 1.1 times the predetermined reflectance of the area of the apparatus detectable means;

said opposed end having a configuration that mates with the asymmetrical insertion end of the strip when the strip is inserted into said apparatus in the first orientation but a configuration that blocks full insertion of the strip when said strip is inserted in a second orientation;

said opposed end having detection means for detecting the apparatus detectable means at the insertion end of said strip only when said strip is fully inserted into said passageway and for producing a signal characteristic of the detection of said apparatus detectable means.

6. The apparatus of claim 5 wherein the apparatus detectable means comprises electrically conductive material and the detection means comprises electrical circuitry detection means.

* * * * *

UNITED STATES PATENT AND TRADEMARK OFFICE
CERTIFICATE OF CORRECTION

PATENT NO. : 5,526,120
DATED : June 11, 1996
INVENTOR(S) : Arvind N. Jina, Loren R. Larson, John L. Smith It is certified that error appears in the above-indentified patent and that said Letters Patent is hereby corrected as shown below:

Column 16, line 4, claim 5, "art" should read -- an --.

Signed and Sealed this

Fourth Day of November, 1997

Attest:

BRUCE LEHMAN

Attesting Officer

Commissioner of Patents and Trademarks